| United States Patent [19] | [11] Patent Number: 4,803,154 |
| Uo et al. | [45] Date of Patent: Feb. 7, 1989 |

[54] MULTI-SPOT ENZYME IMMUNOASSAY METHOD

[75] Inventors: Junko Uo; Masaji Nishimura; Kazuo Horiguchi; Setsuko Nakanishi; Shigeru Kaku, all of Kyoto, Japan

[73] Assignee: Shionogi & Co., Ltd., Osaka, Japan

[21] Appl. No.: 856,018

[22] Filed: Apr. 25, 1986

[30] Foreign Application Priority Data

Apr. 25, 1985 [JP] Japan ................................ 60-90216

[51] Int. Cl.⁴ .......................................... G01N 33/53
[52] U.S. Cl. ........................................ 435/7; 435/301; 435/805; 435/810; 422/56; 436/809
[58] Field of Search ................... 436/809; 435/7, 300, 435/301, 810

[56] References Cited

U.S. PATENT DOCUMENTS

| 3,853,468 | 12/1974 | Haymond | 436/809 |
| 4,055,394 | 10/1977 | Friedman et al. | 436/809 |
| 4,157,895 | 6/1979 | Finlay et al. | 436/809 |
| 4,305,721 | 12/1981 | Bernstein | 436/809 |
| 4,357,142 | 11/1982 | Schall et al. | 436/809 |
| 4,591,570 | 5/1986 | Chang | 436/809 |

*Primary Examiner*—Sam Rosen
*Attorney, Agent, or Firm*—Wenderoth, Lind & Ponack

[57] ABSTRACT

An assay for an immunologically active substance (B) in a biologically derived test sample comprising using an immuno-active membrane of a hydrophobic polymer sheet having numerous hydrophilic spots, on which a prefixed amount of an immuno-active substance (A) or (B) has been immobilized, and a coloring-membrane having numerous spots which contain a color-producing reagent being capable of developing color by the catalytic effect of an enzyme at the corresponding positions to those of the immuno-active membrane, and making contact the immuno-active membrane with said test sample in the presence of an enzyme-labeled immuno-active substance (A') or (B') and a substrate for reacting the substance (A), substance (B) and enzyme-labeled substance (A') or (B') competitively or non-competitively, and superposing the coloring-membrane of on the immuno-active membrane, followed by colorimetrically measuring the resulting color and thereby determining the amount of the substance (B) in the test sample.

12 Claims, 1 Drawing Sheet

MULTI-SPOT ENZYME IMMUNOASSAY METHOD

This invention relates to an enzyme immunoassay, in particular, it relates to a modification in enzyme immunoassays which is practically useful for diagnosis and therapy of various diseases.

BACKGROUND OF THE INVENTION

It is valuable for preventive and therapeutical treatment of various diseases to assay clinically specific active substances including hormones, enzymes, antibodies, etc in biologically derived samples such as blood, urine and cerebrospinal fluids and tissues.

Such a clinical assay is conducted as a routine work in medical centers, hospitals and the like. However, conventional methods usually take a much time, and require relatively a large amount of samples and complicated procedures. These are inconvenient for both patients and those who participate in medical practice. Therefore, it has been desired in medical treatments to develop an assay which requires only a small amount of samples and gives accurate results in a short period of time.

As the clinical assay, there have recently widely been used immunoassays, which are based on the specific reaction between two immunologically active substances, (e.g. an antigen and an antibody), one of which is labeled with a detectable marker. Numerous markers are known for use in immunoassay, for example, enzymes, radioisotopes, fluorophores and the like. Among them, enzymes are especially useful for accuracy because of their substrate specificity. In the case of a typical enzyme immunoassay, a test sample is treated with an immunologically active substance (A) (e.g. an antigen or an antibody) which has previously been labeled with an appropriate enzyme, by which an immunologically active substance (B) (e.g. an antigen or an antibody) contained in the test sample is specifically bound with the substance (A), and then, the enzymatic activity in the bound substance is measured by a conventional method, usually by a colorimetry. The reaction is usually carried out in the presence of an appropriate substrate (e.g. which can be colored by the catalytic effect of said enzyme). According to this method, the amount of the substance (B) in the test sample can quantitatively be determined.

It is well known that the enzyme immunoassay includes "heterogeneous immunoassay" (e.g. "ELISA") and "homogeneous immunoassay" (e.g. "EMIT"). The former employs a phase separation procedure as an integral part of the method, while the latter is conducted in a single reaction mixture. ELISA is applicable to a wide range of substances in comparison with other methods. This invention provides an improvement in ELISA.

ELISA can be classified into two assays by the type of the reaction, that is, a competitive reaction and a non-competitive reaction. In the competitive assay, a test sample containing an unknown amount of an antigen (B) is reacted with a known amount of an immobilized antibody (A) in the presence of an enzyme-labeled antigen (B'), wherein the antigen (B) and the enzyme-labeled antigen (B') are competitively reacted with the immobilized antibody. After the reaction, the immobilized antibody (A)-bound enzyme-labeled antigen (A') is separated from the reaction mixture (usually by decantation), and the catalytic (enzymatic) activity of the bound product is measured. In this competitive reaction, the amount of the enzyme-labeled antigen (B') to be bound to the antibody (A) is decreased by the amount of the antigen (B) contained in the test sample, in other words, the amount of the antigen (B) in the test sample is inversely proportional to the amount of enzyme-labeled antigen (B') which was bound to the immobilized antibody. Accordingly, by measuring the enzymatic activity of the bound enzyme-labeled antigen, there can be measured the amount of the antigen (B) contained in the test sample. On the other hand, in the non-competitive immunoassay (e.g. sandwich assay), an immobilized antibody (A) is firstly contacted with a test sample containing an unknown amount of an antigen (B), and the bound sample is contacted with a known amount of an enzyme-labeled antibody (A'). After the reaction, the bound product of the antigen (B)-the enzyme-labeled antibody (A') is separated from the reaction mixture, and the amount of the bound enzyme-labeled antibody is measured on the basis of the catalytic (enzymatic) activity by a conventional method. The amount of the bound enzyme-labeled antibody is proportional to that of antigen (B) in the test sample. Thus, the amount of the antigen in the test sample can quantitatively be determined.

As mentioned above, these enzyme immunoassays employ an antigen (or antibody) immobilized on the surface of a suitable solid carrier. The solid carriers include various kinds of natural or artificial products, such as polyacrylamides, nylons, glass, etc. In general, porous beads carriers are used in ELISA assay. When the beads carrier is used as a solid phase in ELISA, an immobilized substance (e.g. antigen) which is obtained by fixing the protein on the surface of the beads is reacted with an enzyme-labeled substance (e.g. antibody) competitively or non-competitively. To this reaction mixture, any suitable color-producing reagents such as pigments which can be colored by the catalytic effect of the enzyme is added, and colored reagents are extracted from the reaction mixture. Then, the extract is subjected to the spectrophotometric measurement.

However, the conventional ELISA assay using a solid beads carrier has to be conducted in liquid phases and requires troublesome laboratory procedures such as separation and extraction of colored reagents and spectrophotometrical measurements of the extract. Because of such laboratory procedures, this method can not give the desired data rapidly. It is very important to get rapid and correct informations from these assays instantaneously in order to apply the most suitable diagnoses and treatments to each patient. This is especially significant in case of an emergency. Thus, it has been desired to find an improved immunoassay among people who participate in suitable for clinical assay of diseases, particularly for diagnosis of diseases in the early stage, for instance, in diseases participated by antigen-antibody reaction or various infectious diseases.

OBJECT OF THE INVENTION

Under the circumstances, the present inventors have conducted intensive studies to develop an improved enzyme immunoassay which can measure an immunologically active substance in a living body with a rapid and simple procedure with high accuracy, and have now found that the desired assay can be effected by using a membrane carrier for immobilizing proteins wherein hydrophilic spots are formed in combination of a coloring-membrane on which a pigment is fixed in spots corresponding to the hydrophilic spots of the membrane carrier.

An object of this invention is to provide an improved enzyme immunoassay which can be carried out by a simple procedure and give an accurate result in a short period of time. Another object of this invention is to provide a kit to use in the assay of this invention. These and other objects and advantages of this invention will be apparent to persons skilled in the art from the following description.

DETAILED DESCRIPTION OF THE INVENTION

Figure 1:
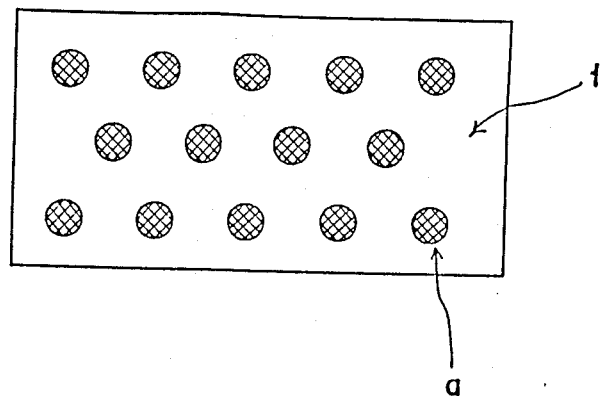
FIG. 1 shows a schematic plain view of one embodiment of an immuno-active membrane with hydrophilic spots used in this invention.

This invention provides a method for the assay of an unknown amount of an immunologically active substance (B) in a biologically derived test sample comprising contacting a prefixed amount of immunologically active substance (A) specifically reactive with the substance (B) or a prefixed amount of an immunologically active substance (B), which is immobilized on a solid carrier, with the test sample containing the substance (B) in the presence of an enzyme-labeled immunologically active substance (A') or (B'), (when the substance (B) is immobilized on a solid carrier, an enzymelabeled immunologically active substance is not (B')), and colorimetrically measuring the amount of the enzyme contained in the enzyme-labeled substance (A') or (B') bound to the immobilized substance (A) or (B), the improvement comprises:

(a) preparing an immuno-active membrane of a hydrophobic polymer sheet having a number of hydrophilic spots, on which a prefixed amount of an immuno-active substance (A) or (B) has been immobilized, (b) preparing a coloring-membrane having a number of spots which contain a color-producing reagent being capable of developing color by the catalytic effect of an enzyme at the corresponding positions to those of the immuno-active membrane, (c) making contact the immuno-active membrane from (a) with said test sample together with an enzyme-labeled immuno-active substance (A') or (B'), simmultaneously or successively, whereby reacting the substance (A), substance (B) and enzyme-labeled substance (A') or(B') competitively or non-competitively, (d) adding dropwise a mixture containing a substrate to each spot of the immuno-active membrane of (c), and (e) superposing the coloring-membrane of (b) on the immuno-active membrane of (d), so that the spots in both membranes corresponds each other, and (f) colorimetrically measuring the resulting color and thereby determining the amount of the substance (B) in the test sample.

The preparation of the immuno-active membrane and the coloring-membrane and further the procedure of this invention are explained in detail below.

(1) Preparation of the immuno-active membrane

The immuno-active membrane used in this invention can be prepared using various kinds of hydrophobic polymers, such as starting materials. The desired number of hydrophilic spots can be formed on the surfaces of the hydrophobic sheets by known procedures in the art. For the purpose of this invention, it is convenient to use a membrane-carrier which has been disclosed in Japanese Patent Application No. 277656/1984 (hereinafter, it is referred to as a "spot-membrane"). That is, a hydrophobic porous polymer sheet such as porous polyolefine sheet (e.g. polypropylene or polyethylene sheet) is put between two shielding boards (e.g. aluminum boards) perforated with numerous small holes (a) of a suitable size. These are exposed to plasma at a low temperature from the both sides of shielding boards. The resulting membrane has numerous hydrophilic spots corresponding to the holes of shielding boards. This membrane is then treated with 0.02–10% aqueous octamethylendiamine in order to promote the immobilization (fixing) of an immuno-active substance (protein) thereon (i.e. amount of proteins adsorbed on a spot depends on the concentration of the octamethylene-diamine). The membrane is washed with phosphate buffer (PB) or phosphate buffered saline (PBS), then treated with glutaraldehyde to introduce aldehyde groups. This membrane is washed again with PB or PBS.

Then, an immuno-active substance is immobilized on the spot-membrane mentioned above by usual methods. This substance is capable of reacting with the substance to be assayed in the test sample, or is its own analogues. For example, when the substance to be assayed (B) is an antigen, the substance to be immobilized may be a known amount of an antibody (B), specific for the substance (A) (include their analogs), vice versa, when the substance (B) is an antibody, the substance to be immobilized (A) is an antigen.

The spot-membrane may be any shape and size, but is conveniently in the shape of a rectangle as shown in the accompanying FIG. 1. The shape may also be square, round or any other shape. The size is also not specified but is in 2 to 12 cm × 6 to 20 cm preferably, 5 cm × 10 cm in view of easy handling. The thickness is usually 25 to 100 cm. The number and size of the spots (a) are also not specified, but the spots are usually formed in 4 to 32 spots per each membrane in a sized of 0.5 to 15 mm in diameter.

This procedure is illustrated in case of using albumin as the test substance (B) (antigen) in the following description.

Firstly, an anti-albumin antibody (A) is prepared as follows.

Animals such as rabbits, goats or guinea-pigs are immunized against albumin by injecting then with a highly purified globulin-free albumin several times. Then, antiserum is harvested from blood samples collected from the immunned animals. An antiseptic agent is added to this antiserum. The anti-albumin antibody (A) may also be a commercially available one. The anti-albumin antibody (A) is diluted with a buffer such as PBS to 1/1500–1/3000 fold. Secondly, the anti-albumin antibody (A) is immobilized onto the spot-membrane as follows. The diluted antibody (A) is added into each spot of the membrane in an amount of 5–100 μl], preferably 10–20 μl]. Alternatively, the spot-membrane may be immersed in 100–1000 μl], preferably 300–400 μl], of the diluted antibody at 4° C.–30° C. for 10 minutes to 48 hours, preferably 5 to 24 hours. After washing with PB or PBS, normal serum from goat, rabbit or guinea-pig, or bovine serum albumin is poured into each spot in order to block unbound groups on the membrane. The resultant membrane is washed again with PB or PBS.

Figure 2:
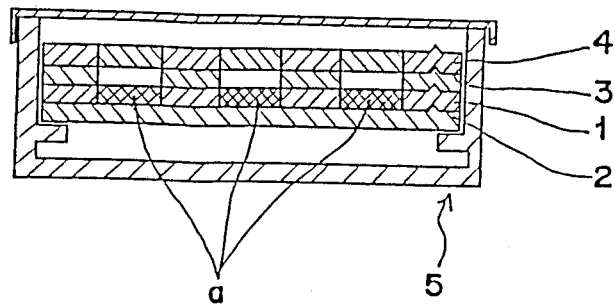
FIG. 2 shows a schematic sectional view of one embodiment of a kit for the enzyme immunoassay of this invention.

The immuno-active membrane may be used as it is, but is preferably used in the form of a kit as shown in the accompanying FIG. 2. That is, the immuno-active membrane (1) is placed on a suitable holding board (2) such as a glass or plastic board (thickness: about 1 mm) and covered with a flame board (3) with holes corresponding to the spots (a) of the immuno-active membrane (1). The holding board (2) is preferably colorless. It will be more convenient to put all of the components (1), (2) and (3) in an appropriate container (5). In FIG. 2, it is shown as attached with a coloring-membrane (4). The thickness of this kit can be 0.5 to 5 mm.

(2) Preparation of coloring membrane

The coloring-membrane is prepared by using the same polymer sheet as used for the spot-membrane as above or a filter paper and the like, wherein a color-producing reagent such as pigment is immobilized at the regions corresponding to those of the spots of the immuno-active membrane. This procedure is illustrated in the following description.

(i) In case of using the same polymer sheet as for the spot-membrane:

The spot-membrane as prepared above without immobilizing an immuno-active substance is adhered to a glass or plastic film such as polyphenylene film with the aid of agar or double-coated adhesive tape. A solution of a pigment (concentration: 0.01–0.1%) in water or 1% agar solution is added to spot in a proportion of 10–20 l/spot. The coloring-membrane should be stored in the dark (under deaeration).

(ii) In case of using a filter paper:

Alternatively, the coloring-membrane can be prepared using filter papers such as TOYO FILTER, No.2, No.131, No.520, or No.514A. The filter paper is dipped in 1 agar containing 0.01–0.1% pigment It is preferred to keep the resultant membrane in the dark and dry condition at the temperature of 25°–37° C. This filter paper is cut into pieces of the same size and shape as the spot on the immuno-active membrane (1). Then, these pieces are adhesively aligned on a suitable support such as glass or polyethylene sheet, preferably colorless one.

(iii) The coloring-membrane can also be prepared from a plate having wells on its surface. This plate may be polyethylene of polypropylene sheet of about 1 mm in thickness. Wells are formed to corresponding to spots on the immuno-active membrane. The previously determined amounts of agar containing a pigment may be added into wells, then the plate is dried. This process is available for many other materials other than agar, for example, gelatin, dextrin and polyethyleneglycol.

Color producing reagents to be used in this invention include many pigments such as 5-aminosalicylic acid, o-phenylenediamine, 2,2'-azyno-di-(3-ethylbenzyl-thiazoline)-6'-sulphonic acid (ABTS), o-nitrophenyl--D-galactoside and phenyl phosphate disodium. The pigment is selected depending on the type of enzyme. For example, when the enzyme is peroxidase (HRP), the pigment may be ABTS, and when the enzyme is $\beta$-D-galactosidase, the pigment may be disodium phenylphosphate.

Immunoassays can be conducted as follows.

(3) Immunological reaction (a) Sandwich assay (non-competitive assay)

An aqueous solution of albumin (B) to be tested (each 50–500 l) is poured into each spot of an immunoactive membrane immobilized with anti-albumin antibody (A) and allowed to react for 10 minutes to 48 hours, preferably, 30 minutes to 3 hours at 4°–30° C., preferably, at 25° C. After or during the reaction, an enzyme-labeled anti-albumin antibody (A') which has been diluted to 1/10–1/3000 with a buffer such as PBS containing surfactants (e.g. Tween) is added to each spot. The membrane is maintained at 4°–37° C., preferably at 30°–35° C. for 10 minutes to 2 hours, preferably 30 to 60 minutes.

(b) Competitive assay

Albumin (B) to be tested and an enzyme-labeled albumin (B') are dissolved in PBS containing surfactants such as Tween, separately. These solutions are combined together in a certain proportion, and the resulting mixture in added to each spot of an anti-albumin antibody (A)-immobilized immuno-active membrane. They are immunologically reacted for 10 minutes to 48 hours at 4°–35° C., preferably, for 10 to 60 minutes at 20°–30° C.

(c) Competitive hindrance assay

An aqueous solution of albumin (B) to be tested is poured into each spot of albumin (B)-immobilized immuno-active membrane. Then, an enzyme-labeled anti-albumin antibody (A) is added thereto. The resulting membrane is treated in the same manner as described in the above (a).

Preferable enzymes for the above enzyme-labeled active substance can be chosed from typically used enzymes in ELISA, for example, horseradish peroxidase (HAP), $\beta$-galactosidase and alkaline phosphatase. The enzyme may be bound to the antigen or antibody to be labeled, by a conventional method such as glutaraldehyde procedure, periodic acid procedure and maleimide procedure.

(4) Determination

The enzyme bound to the immuno-active membrane (1) noncompetitively (3-a) or competitively (3-b and -c) can be detected according to the following steps.

(a) To wash the resultant immuno-active membrane with PB or PBS.

(b) A mixture containing a substrate component other than those immobilized on the coloring-membrane is added dropwise into each spot (a) of the immuno-active membrane (1). The composition of the substrate varies depending on the enzyme. For example, when the enzyme is HRP and the pigment is ABTS, the substrate may be a mixture of 0.003% $H_2O_2$, 0.03 M citric acid and 0.06 M disodium phosphate (pH 4.4).

(c) The coloring membrane (4) is superposed on the immuno-active membrane (1) so that the spots of both membrane correspond each other. In this step, the coloring membrane becomes wet and colored.

(d) After allowing to stand for a while (e.g. 1–10 minutes), the coloring membrane is removed to stop the reaction. Alternatively, about 5 ml of 0.05% sodium azide may be added into each spot (a) to stop the reaction. It is preferable to use an adhesive tape, such as Limbro/Titrek (Plate Seal)®, (manufactured by Floe Laboratories Inc.) or Celotape® (manufactured by Sekisui Chemicals Inc.) for protecting the surface of the coloring membrane (4) against oxidation.

(e) The color of the spots corresponding to the test sample (test spots) is compared to that of the spots which have not been treated with the test sample (control spots) and evaluate their intensity with naked eyes or with the densitometer.

The kit of this invention may be washed by dipping all the components in washing solution such as PBS and draining throughly, and an then used repeatedly. However, when the test sample is infectious, after sealing the container (5), the kit can be discarded.

The assay of this invention is applicable to various ELISA assays, and does not require troublesome laboratory procedures as in conventional assays. This assay is useful to determine a lot of immunologically active substances in biological samples collected from many kinds of organisms, especially human. These substances include hormones, cycloglobulins, growth hormone, insulin, glucagon, human-placental gonadotropins, steroid hormones, and prostaglandin; and further $\alpha$-fetoproteins, tumor fetal antigen, ferritin, IgA, IgM, IgG, IgE, $\alpha_1$-microglobulin, $\beta_2$-microglobulin, basic fetoprotein, HBS antigen, bile acid, various drugs, as well as antibodies caused from bacterial infections or viral infections, and antibodies involved in autoimmune diseases.

According to this invention, a sample can be subjected to an immunological reaction immediately after being collected from subjects such as patients, and accurate results can be obtained in a short period of time.

This invention is significantly useful for diagnoses of various diseases without troublesome laboratory procedures. This means that anyone can conduct the enzyme immunoassay, if necessary.

Since the kit of this invention is portable, immunoassays can be done anywhere and anytime it is needed.

The following examples are provided to further illustrate and examplify the present invention but are in no way intended to limit the scope of the present invention.

EXAMPLE 1

(1) Preparation of spot-membrane

A sheet of plastic membrane (150 mm × 150 mm) was cut off from a commercially available microporous polymer sheet (Juragard ® #2500, 25 μm in thickness, maximum diameter is 0.04–0.4/μm, hydrophobic, manufactured by Polyplastics Inc.), and the sheet was put between two aluminum shielding boards having perforated with 36 holes of 6 mm diameter.

They were subjected to plasma-treatment (100 mA, 500 V) with water vapor for 3 minutes from both sides to , 1 to give a spot-membrane. To this spot-membrane, 5–10 μl of 0.3% aqueous octamethylenediamine was added in each spot and allowed to stand for about 5 minutes. Following the removal of excess liquid, the resultant membrane was immersed in 5% glutaraldehyde solution and washed with distilled water.

(2) Preparation of immuno-active membrane

Rabbit anti-HSA serum (R8411) was diluted with PBS to 1/200. The resultant solution was added to each spot of the spot-membrane obtained in (1) in an amount of 20 μl/spot. The spot-membrane was allowed to stand for 24 hours at 4° C., followed by removal of antiserum with aspirator, and washed. To these spots, HSA labeled with HRP(HRP-HSA) (test spot NO. $B_0$), 10 mg/l of HSA (ibid. $B_{10}$) and 100 mg/l of HSA (ibid. $B_{100}$) were added dropwise, respectively. This membrane was allowed to react at 25° C. for 20 minutes and 40 minutes respectively. The excess of the liquids was removed by aspiration, followed by washing.

(3) Preparation of coloring-membrane

TOYO FILTER PAPER (No.151) was immersed in 1% agar solution containing 0.01% or 0.1% ABT-S(ABTS-agar), then the filter paper was air-dried. This filter paper was cut into many circular pieces (6,φ). These pieces were aligned on the double coated adhesive tape. The Juragard membrane (2500) was attached around the edge of each piece of filter paper. On the piece of filter paper, 15 /μl of substrate solution (0.0034% $H_2O_2$ in 0.03 M citrate-phosphate buffer, pH 4.4 was poured. When the substrate solution was completely diffused, the resulting coloring-membrane was superposed on the immuno-active membrane. They were reacted for 2 to 15 minutes at 25° C. The coloring of the coloring-membrane was measured colorimetrically and evaluated as follows. The results in shown in Table 1. The symbols in the table indicate the observed degree of coloring on a scale of —(not colored) up to +++.

TABLE 1

| Sample No. | $B_0$ | $B_{10}$ | $B_{100}$ | control |
|---|---|---|---|---|
| Degree | +++ | ++ | + | — |

The control assay was conducted using immuno-active membrane containing only HAP-HSA and substrate mixture which lacks $H_2O_2$.

These results indicates that the coloring-membrane develops color corresponding to the concentration of the substances (HSA) in the test sample.

What is claimed is:

1. In a method for the assay of an immunologically active substance (B) in a biologically derived test sample comprising contacting a prefixed amount of an immunologically active substance (A) specifically reactive with the substance (B), which is immobilized on a solid carrier, with the test sample containing the substance (B) in the presence of an enzyme-labelled immunologically active substance (A'), and colorimetrically measuring the amount of the enzyme contained in the enzyme-labelled substance (A') bound to the substance (B) bound to the immobilized substance (A), the improvement which comprises:

(a) preparing an immuno-active membrane of a hydrophobic polymer sheet having a number of hydrophilic spots, on which a prefixed amount of an immuno-active substance (A) has been immobilized, (b) preparing a coloring-membrane having a number of spots which contain a color-producing reagent being capable of developing color by the catalytic effect of an enzyme at the corresponding positions to those of the immuno-active membrane, (c) contacting the immuno-active membrane from (a) with said test sample together with an enzyme-labelled immuno-active substance (A'), simultaneously or successively, thereby reacting the substance (A), substance (B) and enzyme-labelled substance (A') non-competitively, (d) adding dropwise a mixture containing a substrate to each spot of the immuno-active membrane of (c), and (e) superposing the coloring-membrane of (b) on the immuno-active membrane of (d), so that the spots in both membranes correspond to each other, and (f) colorimetrically measuring the resulting color and thereby determining the amount of the substance (B) in the test sample.

2. In a method for the assay of an immunologically active substance (B) in a biologically derived test sample comprising contacting a prefixed amount of an immunologically active substance (A) specifically reactive with the substance (B), which is immobilized on a solid carrier, with the test sample containing the substance (B) in the presence of an enzyme-labelled immunologically active substance (B'), and colorimetrically measuring the amount of the enzyme contained in the enzyme-labelled substance (B') bound to the immobilized substance (A), the improvement which comprises:

(a) preparing an immuno-active membrane of a hydrophobic polymer sheet having a number of hydrophilic spots, on which a prefixed amount of an immuno-active substance (A) has been immobilized.

(b) preparing a coloring-membrane having a number of spots which contain a color-producing reagent being capable of developing color by the catalytic effect of an enzyme at the corresponding positions to those of the immuno-active membrane, (c) contacting the immuno-active membrane from (a) with said test sample together with an enzyme-labelled immuno-active substance (B'), simultaneously or successively, thereby reacting the substance (A), substance (B) and enzyme-labelled substance (B') competitively, (d) adding dropwise a mixture containing a substrate to each spot of the immuno-active membrane of (c), and (e) superposing the coloring-membrane of (b) on the immuno-active membrane of (d), so that the spots in both membranes correspond to each other, and (f) colorimetrically measuring the resulting color and thereby determining the amount of the substance (B) in the test sample.

3. In a method for the assay of an immunologically active substance (B) in a biologically derived test sample comprising contacting a prefixed amount of an immunologically active substance (B), which is immobilized on a solid carrier, with the test sample containing the substance (B) in the presence of an enzyme-labelled immunologically active substance (A'), specifically reactive with the substance (B), and colorimetrically measuring the amount of the enzyme contained in the enzyme-labelled substance (A') bound to the immobilized substance (B), the improvement which comprises:

(a) preparing an immuno-active membrane of a hydrophobic polymer sheet having a number of hydrophilic spots, on which a prefixed amount of an immuno-active substance (B) has been immobilized, (b) preparing a coloring-membrane having a number of spots which contain a color-producing reagent being capable of developing color by the catalytic effect of an enzyme at the corresponding positions to those of the immuno-active membrane, (c) contacting the immuno-active membrane from (a) with said test sample together with an enzyme-labelled immuno-active substance (A'), simultaneously or successively, thereby reacting the substance (B) and enzyme-labelled substance (A') competitively, (d) adding dropwise a mixture containing a substrate to each spot of the immuno-active membrane of (c), and (e) superposing the coloring-membrane of (b) on the immuno-active membrane of (d), so that the spots in both membranes correspond to each other, and (f) colorimetrically measuring the resulting color and thereby determining the amount of the substance (B) in the test sample.

4. The method according to anyone of claims 1 to 3 wherein the hydrophilic spots are circular of 0.5 to 15 mm in diameter.

5. The method according to anyone of claims 1 to 3 wherein the hydrophilic spots are formed on a hydrophobic polymer sheet by means of the plasma-treatment method at a low temperature using oxygen, oxygen-containing gas or water vapor.

6. The method according to anyone of claims 1 to 3 wherein the hydrophobic polymer sheet is porous.

7. The method according to claim 6, wherein the hydrophobic polymer sheet is polyolefin sheet.

8. The method according to claim 7, wherein the polyolefin is polypropylene.

9. The method according to claim 5, wherein the coloring-membrane is prepared by immobilizing a pigment on hydrophilic spots.

10. The method according to claim 6 wherein the coloring-membrane is prepared by immobilizing a pigment on the hydrophilic spots.

11. The method according to claim 7 wherein the coloring-membrane is prepared by immobilizing a pigment on the hydrophilic spots.

12. The method according to claim 8 wherein the coloring-membrane is prepared by immobilizing a pigment on the hydrophilic spots.

* * * * *